United States Patent
Olivier-Bourbigou et al.

(10) Patent No.: US 7,256,152 B2
(45) Date of Patent: *Aug. 14, 2007

(54) COMPOSITION OF CATALYST AND SOLVENT AND CATALYSIS PROCESSES USING THIS COMPOSITION

(75) Inventors: Helene Olivier-Bourbigou, Rueil Malmaison (FR); Dominique Commereuc, Meudon (FR); Olivia Martin, Nanterre (FR); Lionel Magna, Rueil Malmaison (FR); Emmanuel Pellier, Verriere (FR)

(73) Assignee: Institut Francais du Petrole, Cedex (FR)

( * ) Notice: Subject to any disclaimer, the term of this patent is extended or adjusted under 35 U.S.C. 154(b) by 409 days.

This patent is subject to a terminal disclaimer.

(21) Appl. No.: 10/232,837

(22) Filed: Sep. 3, 2002

(65) Prior Publication Data

US 2003/0060359 A1 Mar. 27, 2003

(30) Foreign Application Priority Data

| Aug. 31, 2001 | (FR) | ................... | 01 11398 |
| Jun. 17, 2002 | (FR) | ................... | 02 07454 |
| Aug. 5, 2002 | (FR) | ................... | 02 09920 |
| Aug. 5, 2002 | (FR) | ................... | 02 09921 |

(51) Int. Cl.
- *B01J 31/00* (2006.01)
- *B01J 31/02* (2006.01)
- *B01J 31/14* (2006.01)
- *B01J 35/12* (2006.01)
- *C07B 61/00* (2006.01)
- *C07C 2/00* (2006.01)
- *C07C 2/08* (2006.01)
- *C07C 2/26* (2006.01)
- *C07C 2/62* (2006.01)
- *C07C 5/22* (2006.01)
- *C07C 5/25* (2006.01)
- *C07C 9/21* (2006.01)
- *C07C 11/02* (2006.01)
- *C07C 11/10* (2006.01)
- *C07C 15/02* (2006.01)

(52) U.S. Cl. ............ 502/150; 502/162; 502/164; 502/167; 585/250; 585/253; 585/446; 585/466; 585/502; 585/510; 585/514; 585/520; 585/527; 585/664; 585/667; 585/669; 585/671; 585/709; 585/711; 585/731; 585/732; 585/734

(58) Field of Classification Search ........... 502/162, 502/150, 164, 167; 585/250, 253, 446, 466, 585/502, 510, 514, 520, 527, 664, 667, 669, 585/671, 709, 711, 731, 732, 734

See application file for complete search history.

(56) References Cited

U.S. PATENT DOCUMENTS

| 4,764,440 | A | * | 8/1988 | Jones et al. ............. 429/305 |
| 5,082,956 | A | | 1/1992 | Monnier et al. |
| 5,104,840 | A | * | 4/1992 | Chauvin et al. ............ 502/117 |
| 5,731,101 | A | * | 3/1998 | Sherif et al. ............. 429/102 |
| 6,103,908 | A | * | 8/2000 | Bahrmann et al. ......... 546/347 |
| 6,114,272 | A | * | 9/2000 | Bahrmann ................ 502/164 |
| 6,139,723 | A | * | 10/2000 | Pelrine et al. ............. 208/422 |
| 6,395,948 | B1 | * | 5/2002 | Hope et al. ................ 585/510 |
| 6,515,137 | B2 | * | 2/2003 | MacMillan et al. ........ 548/240 |
| 6,534,434 | B2 | * | 3/2003 | MacMillan et al. ........ 502/167 |
| 6,573,405 | B1 | * | 6/2003 | Abbott et al. ............. 564/292 |
| 6,617,474 | B2 | * | 9/2003 | Favre et al. .............. 568/451 |
| 6,673,737 | B2 | * | 1/2004 | Mehnert et al. ........... 502/159 |
| 6,703,507 | B2 | * | 3/2004 | Bahrmann et al. ........ 546/24 |
| 6,881,698 | B2 | * | 4/2005 | Bonnet et al. ............. 502/162 |
| 6,900,313 | B2 | * | 5/2005 | Wasserscheid et al. ..... 544/59 |
| 2003/0220191 | A1 | * | 11/2003 | Lecocq et al. ............ 502/167 |
| 2003/0225303 | A1 | * | 12/2003 | Magna et al. ............. 568/456 |
| 2004/0045874 | A1 | * | 3/2004 | Olivier-Bourbigou et al. ............... 208/238 |
| 2004/0059153 | A1 | * | 3/2004 | Magna et al. ............. 562/519 |

FOREIGN PATENT DOCUMENTS

WO 00/16902 3/2000

* cited by examiner

*Primary Examiner*—Anthony J. Green
(74) *Attorney, Agent, or Firm*—Millen, White, Zelano & Branigan, P.C.

(57) ABSTRACT

A composition defined:
either as comprising at least one Broensted acid, designated HB, dissolved in a liquid medium with an ionic nature of general formula Q+A−, in which Q+ represents an organic cation and A− represents an anion that is different from B,
or as resulting from dissolving at least one Broensted acid, designated HB, in a non-aqueous liquid medium with an ionic nature of general formula Q+A−, in which Q+ represents an organic cation and A− represents an anion that is identical to the anion B, can be used as a catalyst and solvent in acid catalysis processes, in particular in the alkylation of aromatic hydrocarbons, the oligomerization of olefins, the dimerization of isobutene, the alkylation of olefins by isoparaffins, the isomerization of n-paraffins into isoparaffins, the isomerization of n-olefins into iso-olefins, the isomerization of the double bond of an olefin and the purification of an olefin mixture that contains branched alpha olefins as impurities.

45 Claims, No Drawings

COMPOSITION OF CATALYST AND SOLVENT AND CATALYSIS PROCESSES USING THIS COMPOSITION

BACKGROUND OF THE INVENTION

1. Field of the Invention

This invention relates to a composition that is used as a catalyst and a solvent in acid catalysis processes.

It also relates to acid catalysis processes that use said composition, and more particularly the alkylation of aromatic hydrocarbons, the oligomerization of olefins, the dimerization of isobutene, the alkylation of olefins by isoparaffins, the isomerization of n-paraffins into isoparaffins, the isomerization of n-olefins into iso-olefins, the isomerization of the double bond of an olefin and the purification of a mixture of olefins containing branched alpha olefins as impurities.

2. Description of the Prior Art

The acid catalysis reactions are very important industrial reactions that can be applied in the field of refining and petrochemistry. As an example, the case of the alkylation of aromatic hydrocarbons will be cited, in particular for the production of LABs (for "linear alkyl benzenes"), which are the first intermediate products for the synthesis of biodegradable detergents.

The acid catalysts that are used by the conventional methods, in particular for the alkylation of aromatic hydrocarbons, are Lewis and/or Broensted acids. The most commonly used are hydrofluoric acid (HF), concentrated sulfuric acid ($H_2SO_4$), boron trifluoride ($BF_3$), aluminum trichloride ($AlCl_3$), solid catalysts such as zeolites, or the combination of these different acids. The use of these acids, however, exhibits drawbacks, in particular due to increasingly strict measures aimed at environmental protection. For example, the toxic, volatile and corrosive use of HF involves deploying important safety measures regarding operators and equipment. Low-activity concentrated sulfuric acid requires the use of large volumes of acid that generate waste, essentially inorganic salts, which should be brought under environmental standards before being rejected. Aluminum trichloride, nevertheless more widely used industrially, pure or made complex with a base (often called "red oils"), is consumed in a large amount. In addition, this type of catalyst is not easily separated from the products of the reaction. The recovery of products is then carried out after the catalyst is destroyed, which, on the one hand, generates large amounts of waste, and, on the other hand, is reflected by an additional cost for the process. Consequently, an intensive study for replacing these catalysts is currently being developed.

The solid catalysts such as the zeolites provide an improvement in connection with the separation of the products and the recycling of the catalyst but impose reaction temperatures that are often higher.

In contrast, it is known that the isobutene dimers (trimethyl-2,4,4-pentene-1 and -2) are advantageous intermediate products for the production of different products that have a commercial advantage. By way of examples, it is possible to cite higher alcohols, aldehydes, and acids.

Trimethyl-2,2,4-pentane can be obtained by hydrogenation of trimethylpentenes and constitutes an additive that is sought for the reformulation of gasolines [absence of sulfur, aromatic compound and olefin and low volatility are added to a high octane number: engine octane number (RON) =research octane number (RON)=100].

The selective dimerization of the isobutene, followed by a hydrogenation of the products that are obtained from trimethyl-2,2,4-pentane that have a high octane number, constitutes an advantageous method that makes it possible i. To replace the MTBE (methyl-tert-butyl-ether: RON=118; MON=100), now banned in California for environmental reasons, and ii. To use isobutene, obtained from C4 fractions of the catalytic cracking (FCC) or steam-cracking processes, raw material in the production of MTBE.

The dimerization (oligomerization) of isobutene is an exothermic reaction that is catalyzed by acids. Various acids have been described in literature such as sulfuric acid or its derivatives, chlorinated or fluorinated aluminas, zeolites, silica-aluminas, etc. The acids most typically used in the industry, however, are phosphoric acid (generally supported or "solid phosphoric acid" SAP) and ion-exchange resins ("ion exchange resins" IER, SP-isoether process that is licensed by Snamprogetti or the InAlk process proposed by UOP).

The primary difficulty that is linked to these processes is obtaining a good dimer selectivity. Actually, the exothermicity of the reaction is often difficult to monitor and entrains the formation of oligomers (essentially C12 olefins and C16 olefins) that are obtained by parallel reactions from isobutene. These oligomers have boiling points that are too high and are beyond or at the limit of specifications that are required for reformulated gasolines. Furthermore, these oligomers contribute to deactivating the catalysts.

Various works in literature describe certain solutions for reducing the formation of these oligomers.

In the case of ion-exchange resins (Amberlyst-15 or -35 type), the use of a diluent (or solvent) is often recommended. The selectivity of dimers depends on the choice of this solvent. The most effective additives are alcohols (U.S. Pat. Nos. 5,877,372; 4,100,220) that lead to the co-production of ethers, or the ethers (in U.S. Pat. No. 4,447,668, MTBE, ETBE, etc.). It is possible to cite the works of Snamprogetti (M. Marchionna and al. Catal. Today, 65 (2001) 397-403, GB-A-2 325 237) who studied the influence of the addition of MTBE or MeOH for the purpose of reusing the existing units of MTBE. Advantageous trimethylpentene selectivities can thus be attained but with the conversion of isobutene, the selectivities are often less than 85%.

International Patent Application WO-A-01/51 435 describes a process scheme in which the isobutene is produced by dehydration of tert-butyl alcohol. The isobutene is dimerized preferably by an Amberlyst A-15®-type resin in the presence of tert-butyl alcohol (selectivity promoter) and alkane (butane or isobutane) as a diluent. The presence of occupied alcohol puts the formation of ether at a disadvantage but also reduces the reaction speed.

International Patent Application WO-A-01/46 095 describes a process for producing isooctanes from a C4 fraction with a catalyst that comprises a beta zeolite that makes it possible to convert isobutene selectively in the presence of butenes (conversion of butenes<10%). The C8 selectivities that are described in the examples, however, do not exceed 60%. Furthermore, the service life of the catalyst is not described.

All of the processes that are described above have limitations such as trimethylpentene selectivities that are still too low for high conversions per pass of isobutene, which requires, for example, a recycling of isobutene and increases the cost of the process. The risks of premature deactivation of the catalyst by "fouling" by heavier oligomers or by the impurities that are contained in the feedstocks exist, and the service life of the sulfonic resins is consequently shorter for the production of trimethylpentenes than for the synthesis of MTBE.

It is also known that there is a large variety of catalysts that make it possible to isomerize the double bond of the olefins. This is not surprising, moreover, since it is one of the easiest reactions among the reactions for transformation of the hydrocarbons and since the thermodynamics of the reaction are favorable to the formation of internal olefins at low temperatures. By way of examples, it is possible to cite the isomerization of butene-1 into butene-2 (U.S. Pat. No. 5,237,120 that uses modified zeolites) or else the isomerization of linear alpha olefins (for example C12-C18 in U.S. Pat. No. 4,749,819) for producing internal olefins. However, despite the diversity of existing catalysts, the difficulty remains of carrying out the isomerization of the double bond of the olefin with a good activity without, however, producing (or by reducing the production of) undesirable by-products from oligomers of the olefin.

Finally, numerous industrial processes produce alpha linear olefins that are mixed with internal linear olefins and branched alpha olefins. The branched alpha olefins that are being considered, also called vinylidene olefins, are those that correspond to general formula $CH_2=CRR'$, in which R and R' designate alkyl radicals.

Based on the application (for example the production of detergents, co-monomers for the production of low-density linear polyethylenes—or LLDPE—or precursors for the synthesis of alcohols or aldehydes), it is desirable to have the highest purity possible of linear olefins. The separation of the linear olefins from the branched olefins is not easy, particularly when these olefins have the same molecular weight and similar boiling points. Various patents (U.S. Pat. Nos. 5,789,646; 5,095,172; WO-A-99/29 641) describe the separation of vinylidene olefins from a mixture of linear olefins.

The non-aqueous ionic liquids of composition $Q^+A^-$ are the object of several reviews (for example, T. Welton, Chem. Rev. 1999, 99, 2071). They can be applied in numerous ways as solvents for catalysis by transition metals or as extraction solvents for carrying out liquid-liquid extractions. Their use as solvents and acid catalysts has primarily been described for ionic liquids of organochloroaluminate acid type and applied to the alkylation of aromatic hydrocarbons. Thus, Patent Applications WO-A-95/21806, WO-A-98/03454 and WO-A-00/41809 describe processes for producing alkylaromatic compounds, such as LABs, for example dodecylbenzene from benzene and dodecene, or ethylbenzene by reaction of benzene with ethylene and documents EP-A-693088 and EP-B-576323 of the processes for conversion of olefins by acid catalysis, which, as a whole, use as catalysts non-aqueous ionic liquids that result from bringing into contact quaternary ammonium halides and/or halohydrates of primary, secondary or tertiary amine and/or quaternary phosphonium halides with a Lewis acid such as an aluminum halide, such as, for example, aluminum trichloride. These liquid catalysts can also be, in an improved way, pre-mixed with aromatic hydrocarbon.

The non-aqueous ionic liquids can also be applied to the alkylation of olefins by isobutane (U.S. Pat. No. 5,750,455) or to the production of synthetic lubricants (EP-A-791 643).

The advantage of these liquid catalytic systems is that they are not very miscible with the products of the reaction, whereby the latter can be separated by decanting. The catalytic phase can then be recycled and reused, and the consumption of catalyst is thus reduced. These systems, however, also present limitations. For example, these ionic media are moisture-sensitive. In the presence of protons, the ionic medium can generate hydrochloric acid by reaction with the $AlCl_3$ that is potentially present in the medium, which can entrain the formation of chlorinated organic impurities and can contaminate the products.

Patent Application WO-A-00/16 902 describes the use of an ionic liquid that does not contain the Lewis acidity that is obtained by reaction of a nitrogenous compound (for example an amine or a quaternary ammonium) or phosphorus compound with a Broensted acid in amounts such that the ratio of said nitrogenous compound or phosphorus compound to the acid is less than 1/1. These media are used for catalyzing in particular the alkylation of benzene with decene-1.

SUMMARY OF THE INVENTION

It was now found that the addition of at least one Broensted acid, designated HB, in an ionic liquid with composition $Q^+A^-$ and in which, when A and B are different, results in liquid compositions that can be used as catalysts and solvents for acid catalysis reactions.

It has also be found that these liquid compositions, which are useful as catalysts and solvents for acid catalysis reactions, can be obtained by dissolving at least one Broensted acid, designated HB, in an ionic liquid with composition $Q^+A^-$ and in which Q+ represents an organic cation and A− represents an anion that is identical to the anion B.

By way of examples, it will be possible to use the above mentioned liquid compositions, more particularly for the alkylation of aromatic hydrocarbons, the oligomerization of olefins, the dimerization of isobutene, the alkylation of olefins by isoparaffins, the isomerization of n-paraffins into isoparaffins, the isomerization of n-olefins into iso-olefins, the isomerization of the double bond of an olefin and the purification of a mixture of olefins containing branched alpha olefins as impurities.

The use of these catalyst-solvents exhibits a certain number of advantages. The Broensted acid that is dissolved in the ionic liquid releases a proton that is not very solvated by the medium due to the low nucleophilic capacity of its $A^-$ anions. The force of the Broensted acid, which depends, on the one hand, on its rapidity in releasing a proton (strong acid), and, on the other hand, on the force of solvating this proton by the surrounding medium, is enhanced, which leads to higher activities of acid catalysis.

Furthermore, the products that are formed by the acid catalysis reactions, such as the alkylation of aromatic hydrocarbons, the oligomerization of olefins, the dimerization of isobutene, the alkylation of olefins by isoparaffins, the isomerization of n-paraffins into isoparaffins, and the isomerization of n-olefins into iso-olefins, are in general not very miscible with the ionic liquids that contain the Broensted acid. They can be separated by decanting, and the catalytic phase can be recycled.

In addition, as the solubility in the ionic phase of the primary reaction products is often lower than that of the reagents, these reaction intermediate products are extracted from the catalytic phase as soon as they are formed, before they have even been able to react, consecutively, with another mol of reagent. The selectivities are therefore improved.

DETAILED DESCRIPTION OF THE INVENTION

The object of the invention is a composition that is used as a catalyst and a solvent comprising at least one Broensted acid, designated HB, dissolved in a non-aqueous liquid medium with an ionic nature (medium of the "molten salt" type) of general formula $Q^+A^-$, in which $Q^+$ represents an organic cation and $A^-$ represents an anion that is different from B.

Another object of the invention is a composition resulting from dissolving at least one Broensted acid, designated UB, in a non-aqueous liquid medium with an ionic nature (medium of "molten salt" type) of general formula $Q^+A^-$, in which $Q^+$ represents an organic cation and $A^-$ represents an anion that is identical to the anion B.

The invention also consists in various processes of acid catalysis using said catalytic compositions.

By way of examples, it will be possible to use said composition more particularly for the processes for alkylation of aromatic hydrocarbons, the oligomerization of olefins, the dimerization of isobutene, the alkylation of isobutane by olefins, the isomerization of n-paraffins into isoparaffins, the isomerization of n-olefins into iso-olefins, the isomerization of the double bond of an olefin and the purification of a mixture of olefins containing branched alpha olefins as impurities.

The "molten salt" type medium in which the Broensted acid is dissolved according to the invention has for a general formula $Q^+A^-$ in which $Q^+$ represents a quaternary ammonium and/or a quaternary phosphonium and/or a trialkylsulfonium and $A^-$ represents any known anion as being non-coordinating and able to form a liquid salt at low temperature, i.e., below 150° C.

Anions $A^-$ that can be used within the scope of the invention will preferably be selected from among the following anions: tetrafluoroborate, tetraalkylborates, hexafluorophosphate, hexafluoroantimonate, alkylsulfonates (for example methylsulfonate), perfluoroalkylsulfonates (for example trifluoromethylsulfonate), fluorosulfonate, sulfates, phosphates, perfluoroacetates (for example trifluoroacetate), perfluoroalkylsulfonamides (for example bis-trifluoromethane-sulfonyl amide $N(CF_3SO_2)_2^-$), fluorosulfonamides, perfluoroalkylsulfomethides (for example tris-trifluoromethanesulfonyl methide $C(CF_3SO_2)_3^-$) and carboranes.

The quaternary ammonium and/or phosphonium that are used according to the invention preferably correspond to general formulas $NR^1R^2R^3R^{4+}$ and $PR^1R^2R^3R^{4+}$, or to general formulas $R^1R^2N=CR^3R^{4+}$ and $R^1R^2P=CR^3R^{4+}$ where $R^1$, $R^2$, $R^3$ and $R^4$, identical or different, represent hydrogen with the exception, for $NR^1R^2R^3R^{4+}$, of the cation $NH_4^+$, preferably a single substituent that represents the hydrogen atom, or hydrocarbyl radicals that have 1 to 12 carbon atoms, for example alkyl groups that may or may not be saturated, cycloalkyl groups or aromatic groups, or aryl, alkaryl or aralkyl groups that comprise 1 to 12 carbon atoms. The ammonium and/or phosphonium can also be derived from nitrogenous or phosphorus heterocyclic compounds that comprise 1, 2 or 3 nitrogen atoms and/or phosphorus atoms, of general formulas:

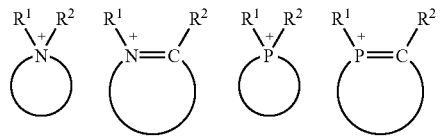

in which the cycles consist of 4 to 10 atoms, preferably 5 to 6 atoms, whereby $R^1$ and $R^2$ are defined as above.

Quaternary ammonium or phosphonium can also consist of a cation that corresponds to one of general formulas:

$$R^1R^{2+}N=CR^3-R^5-R^3C=N^+R^1R^2$$

$$R^1R^{2+}P=CR^3-R^5-R^3C=P^+R^1R^2$$

in which $R^1$, $R^2$ and $R^3$, identical or different, are defined as above, and $R^5$ represents an alkylene or phenylene radical.

Among groups $R^1$, $R^2$, $R^3$ and $R^4$, the radicals methyl, ethyl, propyl, isopropyl, butyl, secondary butyl, tertiary butyl, amyl, methylene, ethylidene, phenyl or benzyl will be mentioned; $R^5$ can be a methylene, ethylene, propylene or phenylene group.

The ammonium and/or phosphonium cation is preferably selected from the group that is formed by N-butylpyridinium, N-ethylpyridinium, butyl-3 methyl-1 imidazolium, diethylpyrazolium, ethyl-3 methyl-1 imidazolium, pyridinium, trimethylphenylammonium, tetrabutylphosphonium and methylethylpyrrolidinium.

The trialkylsulfonium used according to the invention has for a general formula $SR^1R^2R^{3+}$, where $R^1$, $R^2$ and $R^3$, identical or different, represent hydrocarbyl radicals that have 1 to 12 carbon atoms, for example alkyl groups that may or may not be saturated, cycloalkyl or aromatic groups, or aryl, alkaryl or aralkyl groups that comprise 1 to 12 carbon atoms.

By way of examples of ionic liquids that can be used according to the invention, it is possible to cite N-butylpyridinium hexafluorophosphate, N-ethyl pyridinium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, trimethylphenylammonium hexafluorophosphate, butyl-3 methyl-1 imidazolium bis-trifluoromethylsulfonylamide, triethylsulfonium bis-trifluoromethylsulfonylamide, tributylhexylammonium bis-trifluoromethylsulfonylamide, butyl-3 methyl-1 imidazolium trifluoroacetate and butyl-3 dimethyl-1,2 imidazolium bis-trifluoromethylsulfonylamide. These salts can be used alone or mixed. They have a catalyst function and a solvent function.

The Broensted acids that are used according to the invention are defined as being organic acid compounds that can provide at least one proton. These Broensted acids have HB for a general formula, in which B represents an anion.

Anions B are preferably selected from among the following anions: tetrafluoroborate, tetraalkylborates, hexafluorophosphate, hexafluoroantimonate, alkylsulfonates (for example methylsulfonate), perfluoroalkylsulfonates (for example trifluoromethylsulfonate), fluorosulfonate, sulfates, phosphates, perfluoroacetates (for example trifluoroacetate), perfluoroalkylsulfonamides (for example bis-trifluoromethanesulfonyl amide $N(CF_3SO_2)_2^-$), fluorosulfonamides, perfluoroalkylsulfomethides (for example tris-trifluoromethane-sulfonyl methide $C(CF_3SO_2)_3^-$) and carboranes.

The Broensted acids that are used according to the invention can be used alone or in a mixture.

In the formula of Broensted acids that are used according to the invention, B can represent an ion of a chemical nature that is different from that of anion $A^-$ that is present in the ionic liquid.

According to another embodiment, the catalytic composition can result from dissolving at least one Broensted acid HB, wherein B can represent an ion of the same chemical nature as anion $A^-$.

The molar ratio of the Broensted acid to the ionic liquid can be chosen in accordance to the applications for which the catalytic composition is intended. This molar ratio can take any value ranging, for example, up to 30/1.

According to the application for which it is intended, the catalytic composition of the invention can also comprise at least one Lewis acid. The Lewis acids that are being considered are those that are soluble in ionic media. By way of examples, it is possible to cite scandium tris-trifluoromethylsulfonate, ytterbium tris-trifluoromethylsulfonate, scandium tris(bis-trifluoromethanesulfonylamide), aluminum trichloride, zirconium tetrachloride, titanium trichloride, triphenylboron, boron trifluoride and antimony pentafluoride.

If a Lewis acid is used, the concentration of this Lewis acid in the ionic liquid is not critical. It is advantageously from 1 to 500 mmol of Lewis acid compound per liter of ionic liquid, preferably 2 to 200 mmol per liter, and more preferably 2 to 100, even 2 to 50 per liter.

The compounds that are part of the catalytic composition according to the invention can be mixed in any order. The mixing can be done by a simple contact followed by stirring until a homogeneous liquid is formed. This mixing can be done outside of the reactor that is used for the catalytic application or in this reactor.

According to the invention, the catalytic composition as defined above is used more particularly in the acid catalysis processes, in particular the aromatic alkylation processes, and the processes for oligomerization of olefins, dimerization of isobutene, alkylation of isobutane by olefins, isomerization of n-paraffins into isoparaffins and isomerization of n-olefins into iso-olefins and in the processes for isomerization of the double bond of an olefin and purification of a mixture of olefins containing branched alpha olefins as impurities.

In the processes of acid catalysis that use the catalytic composition of the invention, the volumetric ratio between the reagents and the catalytic composition can be 0.1/1 to 1000/1, preferably 1/1 to 100/1. It will be selected so as to obtain the better selectivities.

The temperature at which the reaction is carried out is in general from −50° C. to 200° C.; it is advantageously less than 100° C.

The reaction can be conducted in a closed system, in a semi-open system or continuously with one or more reaction stages. At the outlet of the reactor, the organic phase that contains the reaction products is separated.

In these processes, it is also possible to add to the catalytic composition an organic solvent such as an aliphatic hydrocarbon that is non-miscible or is partially miscible with the ionic liquid that makes possible a better separation of the phases. In a preferred way, the processes are conducted without water.

According to the invention, the acid catalysis process that uses the catalytic compositions that are defined above can consist of a process for alkylation of aromatic hydrocarbons by olefins.

The alkylating agents that can be used are olefins that have, for example, a number of carbon atoms from 2 to 20. These olefins are more particularly ethylene, as well as butenes, hexene-1, octene-1, decene-1, dodecene-1 and tetradecene-1, alone or in a mixture, as they are obtained, for example, in the processes for production of alpha-olefins by oligomerization of ethylene or in the processes for dehydrogenation of paraffins. These olefins can be used in pure or dilute form in an alkane.

In a preferred way, the molar ratio of the Broensted acid to the ionic liquid is less than 1/1, advantageously from 0.01/1 to 1/1.

The catalytic composition that is used in this application can also comprise at least one Lewis acid such as those that are listed above, in the proportions that are indicated.

The molar ratio between the olefin and the aromatic hydrocarbon can go from 0.05/1 to 100/1, and preferably from 0.1/1 to 10/1.

The reaction can be done with or without the presence of the vapor phase and the pressure is the autogenic pressure; the latter can also be increased up to 100 MPa.

The reaction period, which depends on the temperature, is between 1 minute and 10 hours. It is adjusted to find a good compromise between conversion and selectivity.

According to the invention, the acid catalysis process that uses the catalytic compositions that are defined above can also consist of a process for dimerization of olefins and in particular for dimerization of isobutene.

In a preferred way, the molar ratio of the Broensted acid to the ionic liquid is less than 0.1/1, for example from 0.001/1 to 0.1/1.

The dimerization reaction can be carried out in the presence of an alcohol or an ether.

It can also be conducted according to a reactive distillation technique.

The products that are obtained by this process can be transformed later according to different reactions, such as hydrogenation, hydroformylation, oxidation, etherification, epoxidation or hydration.

The acid catalysis process using the catalytic compositions that are defined above can also consist of a process for oligomerization of olefins.

This process is applied in a general manner to the olefins of 4 to 20 carbon atoms.

In a preferred way, the molar ratio of the Broensted acid to the ionic liquid is in general less than 1/1, preferably 0.1/1 to 1/1.

The catalytic composition that is used in this application can also comprise at least one Lewis acid such as those that are listed above, in the indicated proportions.

The acid catalysis process using the catalytic compositions that are defined above can also consist of a process for isomerization of the double bond of an olefin.

This process applies to olefins that have from 4 to 30 atoms of pure carbon or in a mixture.

In a preferred way, the molar ratio of the Broensted acid to the ionic liquid is less than 1/1, preferably 0.001/1 to 1/1.

The reaction can be conducted according to a reactive distillation technique.

The acid catalysis process using the catalytic compositions that are defined above can also consist of a process for purification of a mixture of olefins that contain as impurities branched alpha olefins—also called vinylidene olefins—that correspond to the general formula $CH_2=CRR'$, in which R and R' designate alkyl radicals.

This process is applied to feedstocks that contain a mixture of olefins having 4 to 30 carbon atoms. The proportion of vinylidene olefins contained in the mixture is in general between 0.05% and 50% and preferably between 0.05% and 10%.

In a preferred way, the molar ratio of the Broensted acid to the ionic liquid is less than 1/1, preferably 0.001/1 to 0.1/1.

The process can be conducted according to a reactive distillation technique.

The acid catalysis process using the catalytic compositions that are described above can also consist of a process for the production of paraffinic hydrocarbons by alkylation reaction of at least one olefin with an isoparaffin.

The isoparaffins that can be used according to this process are more particularly isobutane, methyl-2 butane, and methyl-2 and methyl-3-pentanes.

The olefins that can be used according to this process are more particularly ethylene, propylene, n-butenes, isobutene, n-pentenes and isopentenes.

The isoparaffin and the olefin can be introduced separately or in a mixture. The molar ratio of the isoparaffin to the olefin is, for example, 2/1 to 100/1 and more advantageously 10/1 to 50/1, preferably 5/1 to 20/1.

In a preferred way, the temperature of the reaction is between −20° C. and +30° C.

In a preferred way, the molar ratio of the Broensted acid to the ionic liquid can be greater than 1/1, preferably 1/1 to 30/1.

The catalytic composition that is used according to the invention can also comprise at least one Lewis acid such as those that are listed above, in the indicated proportions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The following examples illustrate the invention without limiting its scope.

1/Aromatic Alkylation

EXAMPLE 1-1

Preparation of a Catalytic System

At ambient temperature, under inert atmosphere of the glove box, 2.46 g (5.87 mmol) of butyl-1 methyl-3 imidazolium bis(trifluoromethylsulfonyl)amide ($BMI^+NTf_2^-$)—prepared from butyl-1 methyl-3 imidazolium chloride and lithium bis(trifluoromethylsulfonyl)amide as described by M. Grätzel in *Inorganic Chemistry*, 1996, 143, 1168—is mixed with 0.907 g (3.22 mmol) of $HNTf_2$ acid that was previously sublimed. The mixture is stirred for several minutes and results in a colorless, clear solution.

EXAMPLE 1-2

Alkylation of O-xylene

A mixture that contains 4.35 ml (35.65 mmol) of o-xylene and 0.6 ml (4.77 mmol) of hexene-1, both previously distilled, is introduced at ambient temperature and under argon atmosphere into a Schlenk tube that contains 3.03 g of the catalytic mixture that is prepared in Example 1-1. The olefin-aromatic hydrocarbon mixture forms an upper phase that is non-miscible in ionic liquid. It is stirred vigorously with a bar magnet at ambient temperature. At the end of 3 hours, the stirring is stopped, and an aliquot of the supernatant phase is taken that is analyzed by gas-phase chromatography. 98% of hexene-1 was converted into a mixture that contains 54% of mono-alkylation products and 0.3% of di-alkylation products, whereby the remainder is a mixture of hexenes-2 and hexenes-3.

EXAMPLE 1-3

Reuse of the System of Example 1-2

The entire supernatant organic phase of Example 1-2 is drawn off. A mixture that contains 3.89 ml (31.87 mmol) of o-xylene and 0.6 ml (4.70 mmol) of hexene-1, both previously distilled, is added. The operation is performed as in Example 1-2. At the end of 3 hours, the stirring is stopped, and an aliquot of the supernatant phase is taken that is analyzed by gas-phase chromatography. 93% of hexene-1 was converted into a mixture that contains 48% mono-alkylation products and 0.6% di-alkylation products, whereby the remainder is a mixture of hexenes-2 and hexenes-3.

2/Dimerization

EXAMPLE 2-1

Preparation of the $BMI-CF_3SO_3/HN(CF_3SO2)_2$ Catalytic System

At ambient temperature, under inert atmosphere, 8.50 g (6 ml) of butyl-1 methyl-3 imidazolium ($BMI^+CF_3SO_3^-$) trifluoromethylsulfonate (triflate $CF_3SO_3^-$) that contains 25 ppm of water—prepared from butyl-1-imidazole and methyl triflate—was mixed with 0.23 g (0.82 mmol) of bis-triflylamide acid $HN(CF_3SO_2)_2$. The mixture is stirred for several minutes and results in a clear solution that contains 2.7% by weight of acid.

EXAMPLE 2-2

Dimerization of Isobutene Using the Catalytic Composition of Example 2-1

The entire mixture that is prepared in Example 2-1 is introduced under argon atmosphere into a Fisher-Porter tube with a volume of 50 ml, equipped with a bar magnet and previously oven-dried and drawn off in a vacuum. Then, at ambient temperature, 30 ml of a liquid feedstock that contains 95% isobutene and 5% n-butane is introduced. The stirring is then begun (zero-time of the reaction). The reaction starts up. After 52 minutes of reaction at 25° C., the stirring is stopped. The gas phase is totally recovered and analyzed by CPV (PONA column, isotherm 25° C.). 85% of the initial isobutene was converted. The supernatant organic phase is separated from the ionic liquid phase and analyzed by CPV (with heptane as an external standard) after treatment with soda (10N) to eliminate possible traces of acid and drying on $MgSO_4$. It consists of 83% of trimethyl-2,4,4-pentenes and 16% trimers (C12).

EXAMPLE 2-3

Preparation of the $BMI\text{-}CF_3SO_3/CF_3SO_3H$ Catalytic System

At ambient temperature, under inert atmosphere, 8.50 g (6 ml) of butyl-1 methyl-3 imidazolium ($BMI^+CF_3SO_3^-$) trifluoromethylsulfonate (triflate $CF_3SO_3^-$) that contains 25 ppm of water—prepared from butyl-1-imidazole and methyl triflate—was mixed with 0.12 g (0.8 mmol) of triflic acid ($CF_3SO_3H$). The mixture is stirred for several minutes and results in a clear solution that contains 1.4% by weight of acid.

EXAMPLE 2-4

Dimerization of the Isobutene Using the Catalytic Composition of Example 2-3

The entire mixture that is prepared in Example 2-3 is introduced, under argon atmosphere, into a Fisher-Porter tube with a volume of 50 ml, equipped with a bar magnet and previously oven-dried and drawn off in a vacuum. Then, at ambient temperature, 30 ml of a liquid feedstock that contains 95% isobutene and 5% butane is introduced. The stirring is then begun (zero-time of the reaction). The reaction starts up. After 95 minutes of reaction at 25° C., the stirring is stopped. The gas phase is totally recovered and analyzed by CPV (PONA column, isotherm 25° C.). 79% of the initial isobutene was converted. The supernatant organic phase is separated from the ionic liquid phase and analyzed as in Example 2-2. It consists of 86% trimethyl-2,4,4-pentenes and 14% trimers (C12).

EXAMPLE 2-5

Reuse of the System of Example 2-4

The entire supernatant organic phase of Example 2-4 is drawn off. 30 ml of a feedstock that consists of 95% isobutene and 5% n-butane is added. The operation is performed as in Example 2-4. After 12 minutes of reaction, the conversion of isobutene is 36%, and the dimer selectivity is 88%.

EXAMPLE 2-6

Reuse of the System of Example 2-5

The entire supernatant organic phase of Example 2-5 is drawn off. 30 ml of a feedstock that consists of 95% isobutene and 5% n-butane is added. The operation is performed as in Example 2-4. After 45 minutes of reaction, the conversion of the isobutene is 67%, and the dimer selectivity is 89%.

EXAMPLE 2-7

Reuse of the System of Example 2-6

The entire supernatant organic phase of Example 2-6 is drawn off. 30 ml of a feedstock that consists of 95% isobutene and 5% n-butane is added. The operation is performed as in Example 2-4. After 95 minutes of reaction, the conversion of isobutene is 70%, and the dimer selectivity is 88%.

EXAMPLE 2-8

Reuse of the System of Example 2-7

The entire supernatant organic phase of Example 2-7 is drawn off. 30 ml of a feedstock that consists of 95% isobutene and 5% n-butane is added to the mixture. The operation is performed as in Example 2-4. After 95 minutes of reaction, the conversion of the isobutene is 67%, and the dimer selectivity is 89%.

EXAMPLE 2-9

Reuse of the System of Example 2-8

The entire supernatant organic phase of Example 2-8 is drawn off. 30 ml of feedstock that consists of 95% isobutene and 5% n-butane is added. The operation is performed as in Example 2-4. After 95 minutes of reaction, the conversion of isobutene is 68%, and the dimer selectivity is 88%.

EXAMPLE 2-10

Dimerization of an Isobutene-butene-1 Mixture

A mixture that is identical to the one that is described in Example 2-3 is prepared. 8.50 g (6 ml) of this mixture is injected into a Fisher-Porter-type tube. A liquid feedstock (30 ml) that contains 3.3% n-butane, 48.2% butene-1 and 48.5% isobutene is then introduced. The procedure is performed as in Example 2-4. After 150 minutes of reaction, the analysis of the gas phase is carried out by vapor-phase chromatography (CPV). The conversion of isobutene is 86%, and the conversion of butene-1 into co-dimers is 5.1%. 0.7% of butene-1 is isomerized into butenes-2. The liquid phase is separated and analyzed. It consists of 82% dimers, 17% trimers and 1% tetramers.

EXAMPLE 2-11

Reuse of the Salt of Example 2-10

The entire supernatant organic phase of Example 2-10 is drawn off. 30 ml of a feedstock that is identical to the one that is used in Example 2-10 is added. After 150 minutes of reaction, the conversion of isobutene is 86%, and the conversion of butene-1 into co-dimers is 2.9%. 0.7% of butene-1 is isomerized into butenes-2. The liquid phase is separated and analyzed. It consists of 82% dimers, 17% trimers and 1% tetramers.

EXAMPLE 2-12

Reuse of the Salt of Example 2-11

The entire supernatant organic phase of Example 2-11 is drawn off. 30 ml of a feedstock that is identical to the one that is used in Example 2-10 is added. After 150 minutes of reaction, the conversion of isobutene is 84%, and the conversion of butene-1 into co-dimers is 0.7%. 0.6% of the butene-1 is isomerized into butenes-2. The liquid phase is separated and analyzed. It consists of 85% dimers, 14% trimers and less than 1% tetramers.

EXAMPLE 2-13

Reuse of the Salt of Example 2-12

The entire supernatant organic phase of Example 2-12 is drawn off. 30 ml of a feedstock that is identical to the one that is used in Example 2-10 is added. After 150 minutes of reaction, the conversion of isobutene is 85%, and the conversion of butene-1 into co-dimers is 0.7%. 0.7% of butene-1 is isomerized into butenes-2. The liquid phase is separated and analyzed. It consists of 86% dimers, 13% trimers and less than 0.5% tetramers.

EXAMPLE 2-14

Preparation of the BMI-N($CF_3SO_2$)$_2$/HN($CF_3SO_2$)$_2$ Catalytic System 6 ml of a butyl-1-methyl-3-imidazolium bis-trifluoromethylsulfonylamide ionic liquid (BMI-NTf$_2$) was prepared by reaction of one equivalent of lithium salt (LiNTf$_2$) with butyl-1-methyl-3-imidazolium chloride in water as described in the literature. To this salt, 1 mg (0.004 mmol) of HNTf$_2$ acid was added. A liquid at ambient temperature that contains 0.01% by weight of acid was obtained.

EXAMPLE 2-15

Dimerization of Isobutene Using the BMI-N($CF_3SO_2$)$_2$/HN($CF_3SO_2$)$_2$ Catalytic System 30 ml of a liquid feedstock that contains 95% isobutene and 5% butane (as in Example 2-2) is added to the mixture prepared in Example 2-14. The stirring is then begun (zero-time of the reaction). The reaction starts up. After 95 minutes of reaction at 25° C., the stirring is stopped. The gas phase is totally recovered and analyzed by vapor-phase chromatography (CPV: PONA column, isotherm 25° C.). 76% of the initial isobutene was converted. The supernatant organic phase is separated. It consists of 77% trimethyl-2,4,4-pentenes and 20% trimers (C12).

3/Oligomerization.

EXAMPLE 3-1

Preparation of the [BMI][($CF_3SO_2$)$_2$N]/HN($CF_3SO_2$)$_2$ Catalytic System (70/30 by Weight)

At ambient temperature, under inert atmosphere, 6.42 g (15.3 mmol) of butyl-1-methyl-3-imidazolium bis(trifluoromethylsulfonyl)amide ([BMI]$^+$[($CF_3SO_2$)$_2$N]$^-$) that contains 10 ppm of water—prepared from butyl-1-methyl-3-imidazolium chloride and lithium bis(trifluoromethylsulfonyl)amide—was mixed with 2.74 g (9.75 mmol) of bistriflylamide acid ($CF_3SO_2$)$_2$NH. The mixture is stirred for several minutes and results in a clear solution that contains 29.91% by weight of acid.

EXAMPLE 3-2

Isobutene/Butene-1 Oligomerization with the Composition of Example 3-1

6 ml (or 9.16 g) of the mixture that is prepared in Example 3-1 is introduced, under argon atmosphere, into a Fisher-Porter tube with a volume of 50 ml, equipped with a bar magnet and previously oven-dried and drawn off in a vacuum. Then, at ambient temperature, 30 ml of a liquid feedstock that contains 48.5% isobutene, 48.2% butene-1 and 3.3% n-butane (internal standard) is introduced. The stirring is then begun (zero-time of the reaction). The start-up of the reaction is reflected by an increase of the temperature of the system up to 52.9° C. After 35 minutes of reaction, the stirring is stopped. The gas phase is totally recovered and analyzed by CPV (PONA column, isotherm 25° C.). 99% of the isobutene and 51.2% of initial butene-1 were converted. The supernatant organic phase is separated from the ionic liquid phase and treated with soda (10N) to eliminate possible traces of acid. After drying on MgSO4, the organic phase is analyzed by CPV (with heptane as an external standard). This phase consists of 28.0% dimers, 51.3% trimers, 19.8% tetramers and 0.9% pentamers.

EXAMPLE 3-3

Reuse of the System of Example 3-2

The entire supernatant organic phase of Example 3-2 is drawn off. 30 ml of a feedstock that consists of 48.5% isobutene, 48.2% butene-1 and 3.3% n-butane is added. The operation is performed as in Example 3-2. After 48 minutes of reaction, the conversion of isobutene is 97.8%, and that of butene-1 is 19.7%. The reaction products are at 32.5% of the dimers, 49.1% of the trimers, 16.0% of the tetramers and 2.4% of the pentamers.

4/Isomerization of the Double Bond

EXAMPLE 4-1

Preparation of the [BMI][($CF_3SO_2$)$_2$N]/HN($CF_3SO_2$)$_2$ Catalytic System (70/30 by Weight)

At ambient temperature, under inert atmosphere, 5.095 g (3.5 ml) of butyl-1-methyl-3-imidazolium bis(trifluoromethylsulfonyl)amide ([BMI]$^+$[($CF_3SO_2$)$_2$N]$^-$) that contains 10 ppm of water—prepared from butyl-1-methyl-3-imidazolium chloride and lithium bis(trifluoromethylsulfonyl)amide—was mixed with 2.19 g (7.79 mmol) of HN($CF_3SO_2$)$_2$ acid. The mixture is stirred for several minutes and results in a clear solution that contains 30.06% by weight of acid.

EXAMPLE 4-2

Isomerization of Hexene-1 with the Composition of Example 4-1 at 20° C.

3.5 ml of the mixture that is prepared in Example 4-1 is introduced, under argon atmosphere, into a Schlenk tube with a volume of 30 ml, equipped with a bar magnet and previously oven-dried and drawn off in a vacuum. Then, at ambient temperature, 2 ml of heptane (internal standard) and 5 ml of hexene-1 (3.365 g, 40 mmol) are introduced. The stirring is then begun (zero-time of the reaction), and the temperature is kept at 20° C. After 5 hours of reaction at 20° C., the supernatant organic phase is separated from the ionic liquid phase and analyzed by CPV (PONA column). The conversion of hexene-1 reaches 92.9%. The reaction products consist of 57.8% trans-2-hexene, 22% cis-3-hexene, 19.7% cis-2-hexene and 0.5% trans-3-hexene.

EXAMPLE 4-3

Isomerization of Hexene-1 with the Composition of Example 4-1 at 40° C.

3.5 ml of the mixture prepared in Example 4-1 is introduced, under argon atmosphere, into a Schlenk tube with a volume of 30 ml, equipped with a bar magnet and previously oven-dried and drawn off in a vacuum. Then, at ambient temperature, 2 ml of heptane (internal standard) and 5 ml of hexene-1 (3.365 g, 40 mmol) are introduced. The system is then brought to 40° C. before beginning the stirring (zero-time of the reaction). After 5 hours of reaction at 40° C., the supernatant organic phase is separated from the ionic liquid phase and analyzed by CPV (PONA column). The conversion of hexene-1 reaches 98.6%. The reaction products consist of 59.2% trans-2-hexene, 23.6% cis-3-hexene, 16.7% cis-2-hexene and 0.4% trans-3-hexene.

EXAMPLE 4-4

Isomerization of Hexene-1 with the Composition of Example 4-1 at 50° C.

3.5 ml of the mixture that is prepared in Example 4-1 is introduced, under argon atmosphere, into a Schlenk tube with a volume of 30 ml, equipped with a bar magnet and previously oven-dried and drawn off in a vacuum. Then, at ambient temperature, 2 ml of heptane (internal standard) and 5 ml of hexene-1 (3.365 g, 40 mmol) are introduced. The system is then brought to 50° C. before the stirring is begun (zero-time of the reaction). After 5 hours of reaction at 50° C., the supernatant organic phase is separated from the ionic liquid phase and analyzed by CPV (PONA column). The conversion of hexene-1 reaches 98.8%. The reaction products consist of 58.6% trans-2-hexene, 23.6% cis-3-hexene, 17.3% cis-2-hexene and 0.5% trans-3-hexene.

5/Purification of Linear Olefins

EXAMPLE 5-1

Preparation of the $[BMI][(CF_3SO_2)_2N]/HN(CF_3SO_2)_2$ Catalytic System (99.81/0.19 by Weight)

7.27 g (5 ml) of butyl-1-methyl-3-imidazolium bis(trifluoromethylsulfonyl)amide ($[BMI][(CF_3SO_2)_2N]$) containing 10 ppm of water—prepared from butyl-1-methyl-3-imidazolium chloride and lithium bis(trifluoromethylsulfonyl)amide—was mixed with 0.014 g (0.005 mmol) of bis-triflylamide acid $HN(CF_3SO_2)_2$. The mixture is stirred for several minutes and results in a clear solution that contains 0.19% by weight of acid.

EXAMPLE 5-2

Treatment of the Hexene-1/ethyl-2-butene-1 Mixture with the Composition of Example 5-1

3 ml of the mixture that is prepared in Example 5-1 is introduced, under argon atmosphere, into a Schlenk tube with a volume of 30 ml, equipped with a bar magnet and previously oven-dried and drawn off in a vacuum. Then, at ambient temperature, 2 ml of heptane (internal standard) and 5 ml of a mixture containing 96.4% hexene-1 and 3.6% ethyl-2-butene-1 by weight are introduced. The temperature of the reaction is kept at 20° C. The beginning of the stirring constitutes the zero-time of the reaction. After 1 hour of reaction at 20° C., the supernatant organic phase is separated from the ionic liquid phase and analyzed by CPV (PONA column). The conversion of hexene-1 is 0.3% (isomerization). Ethyl-2-butene-1 is converted at 100% into ethyl-2-butene-2. The product that is obtained can then be distilled. More than 98% of hexene-1 that no longer contains ethyl-2-butene-1 is recovered.

EXAMPLE 5-3

Preparation of a $[BMI][(CF_3SO_2)_2N]/HN(CF_3SO_2)_2$ Catalytic System (97.06/2.94 by Weight)

7.27 g (5 ml) of butyl-1-methyl-3-imidazolium bis(trifluoromethylsulfonyl)amide ($[BMI][(CF_3SO_2)_2N]$) containing 10 ppm of water—prepared from butyl-1-methyl-3-imidazolium chloride and lithium bis(trifluoromethylsulfonyl)amide—was mixed with 0.22 g (0.78 mmol) of bis-triflylamide acid $HN(CF_3SO_2)_2$. The mixture is stirred for several minutes and results in a clear solution containing 2.94% by weight of acid.

EXAMPLE 5-4

Treatment of the Hexene-1/ethyl-2-butene-1 Mixture with the Composition of Example 5-3

3 ml of the mixture prepared in Example 5-3 is introduced, under argon atmosphere, into a Schlenk tube with a volume of 30 ml, equipped with a bar magnet and previously oven-dried and drawn off in a vacuum. Then, at ambient temperature, 2 ml of heptane (internal standard) and 5 ml of a mixture containing 96.6% hexene-1 and 3.4% ethyl-2-butene-1 by weight are introduced. The temperature of the reaction is kept at 20° C. The beginning of the stirring constitutes the zero-time of the reaction. After 1 hour of reaction at 20° C., the supernatant organic phase is separated from the ionic liquid phase and analyzed by CPV (PONA column). The hexene-1 is converted at 8% into hexenes-2 and hexenes-3. The ethyl-2-butene-1 is converted at 100% into C12 olefins (45%) and into ethyl-2-butene-2 (55%).

6/Aliphatic Alkylation

EXAMPLE 6-1

Preparation of the $[BMI][(CF_3SO_2)_2N]/CF_3SO_3H$ Catalytic System

At ambient temperature, under inert atmosphere, 3.74 g (8.9 mmol) of butyl-1-methyl-3-imidazolium bis(trifluoromethylsulfonyl)amide ($[BMI]^+[(CF_3SO_2)_2N]^-$) containing 11 ppm of water—prepared from butyl-1-methyl-3- imidazolium chloride and lithium bis(trifluoromethylsulfonyl)amide—was mixed with 15.4 g (102.7 mmol) of trifluoromethanesulfonic acid. The mixture is stirred for several minutes and results in a clear solution that contains 80.5% by weight of acid.

EXAMPLE 6-2

Alkylation of Butene-2 by Isobutane with the Composition of Example 6-1

7 ml of the mixture prepared in Example 6-1 and a mixture containing 103 ml of isobutane and 11 ml of n-butane (standard) are introduced, under argon atmosphere, into a Fisher-Porter tube with a volume of 125 ml, equipped with a bar magnet and previously dried at 100° C. and drawn off in a vacuum. It is cooled to −15° C., then 16 ml of butene-2 is introduced in 15 minutes per fraction of 4 ml. After 2 hours of reaction, the gaseous phase is recovered, quantified and analyzed by CPG. The supernatant organic phase is decanted and separated with a nozzle and then weighed. It is also analyzed after neutralization with soda by CPG (PONA column). The total balance results in the following product distribution: 28% of hydrocarbons less than C8, 52% of C8 (compounds with 94% 2,2,4-trimethylpentane) and 20% of hydrocarbons greater than C8.

The entire disclosures of all applications, patents and publications, cited herein and of corresponding French Application No. 0111398, filed Aug. 31, 2001, French Application No. 0207454, filed Jun. 17, 2002, French Application No. 0209920, filed Aug. 5, 2002, French Application No. 0209921, filed Aug. 5, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalytic composition, comprising at least one Bronsted acid, designated HB, dissolved in a non-aqueous liquid medium with an ionic nature of formula $Q^+A^-$, in which $Q^+$ represents an organic cation and $A^-$ represents an anion that is different from B.

2. A catalytic composition according to claim 1, wherein in formula $Q^+A^-$, anion $A^-$ is selected from the group consisting of the following anions: tetrafluoroborate, tetraalkylborates, hexafluorophosphate, hexafluoroantimonate, alkylsulfonates, perfluoroalkylsulfonates, fluorosulfonate, sulfates, phosphates, perfluoroacetates, perfluoroalkylsulfonamides, fluorosulfonamides, perfluoroalkylsulfomethides and carboranes.

3. A catalytic composition according to claim 1, wherein in formula $Q^+A^-$, $Q^+$ represents at least one cation selected from the group consisting of a quaternary ammonium, a quaternary phosphonium and a trialkylsulfonium, and $A^-$ represents any non-coordinating anion able to form with $Q^+$ a liquid salt at below 150° C.

4. A catalytic composition according to claim 3, wherein $Q^+$ is at least a compound of formulae selected from the group consisting of:
$NR^1R^2R^3R^{4+}$, $PR^1R^2R^3R^{4+}$, $R^1R^2N=CR^3R^{4+}$ and $R^1R^2P=CR^3R^{4+}$, where $R^1$, $R^2$, $R^3$ and $R^4$, identical or different, represent hydrogen or hydrocarbyl radicals having 1 to 12 carbon atoms with the exception, for $NR^1R^2R^3R^{4+}$, only one of $R^1$, $R^2$, $R^3$ and $R^4$ substituents represents hydrogen, a quaternary ammonium and/or phosphonium cation derived from nitrogenous or phosphorus heterocyclic compounds comprising 1, 2 or 3 nitrogen atoms and/or phosphorus atoms, of the formula:

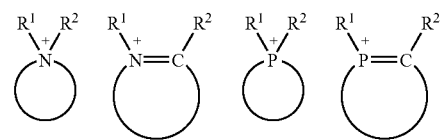

in which the cycles consist of 4 to 10 atoms, wherein $R^1$ and $R^2$ are defined as above;

a quaternary ammonium and/or phosphonium cation of formula:

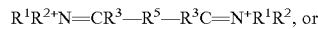

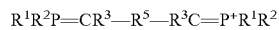

in which $R^1$, $R^2$ and $R^3$, identical or different, are defined as above, and $R^5$ represents an alkylene radical or a phenylene radical.

5. A catalytic composition according to claim 4, wherein $Q^+$ is selected from the group consisting of by N-butylpyridinium, N-ethylpyridinium, butyl-3 methyl-1 imidazolium, diethylpyrazolium, ethyl-3 methyl-1 imidazolium, pyridinium, trimethyl-phenylammonium, tetrabutylphosphonium and methylethylpyrrolidinium.

6. A catalytic composition according to claim 3, wherein $Q^+$ corresponds to formula $SR^1R^2R^{3+}$, wherein $R^1$, $R^2$ and $R^3$, identical or different, represent hydrocarbyl radicals that have 1 to 12 carbon atoms.

7. A catalytic composition according to claim 1, wherein the ionic liquid is selected from the group consisting of N-butylpyridinium hexafluorophosphate, N-ethyl pyridinium tetrafluoroborate, butyl-3 methyl-1 imidazolium hexafluoroantimonate, butyl-3 methyl-1 imidazolium hexafluorophosphate, butyl-3 methyl-1 imidazolium trifluoromethylsulfonate, pyridinium fluorosulfonate, trimethylphenyl-ammonium hexafluorophosphate, butyl-3 methyl-1 imidazolium bis-trifluoromethylsulfonylamide, triethylsulfonium bis-trifluoromethylsulfonylamide, tributylhexylammonium bis-trifluoromethyl-sulfonylamide, butyl-3 methyl-1 imidazolium trifluoroacetate and butyl-3 dimethyl-1,2 imidazolium bis-trifluoromethylsulfonylamide, butyl-3 methyl-1 imidazolium bis-trifluoromethylsulfonylamide and trifluoromethylsulfonate.

8. A catalytic composition according to claim 1, wherein anion B of the Bronsted acid is selected from the group consisting of the following anions: tetrafluoroborate, tetraalkylborates, hexafluorophosphate, hexafluoroantimonate, alkylsulfonates, methylsulfonate, perfluoroalkylsulfonates, trifluoromethylsulfonate, fluorosulfonate, sulfates, phosphates, perfluoroacetates, trifluoroacetate, perfluoroalkylsulfonamides, bis-trifluorornethanesulfonyl amide $N(CF_3SO_2)_2^-$, fluorosulfonamides, perfluoroalkylsulfomethides, tris-trifluoromethane-sulfonyl methide $C(CF_3SO_2)_3^-$ and carboranes, bis-trifluoromethanesulfonylamide $N(CF_3SO_2)_2^-$ and tris -trifluoromethane-sulfonyl methide $C(CF_3SO_2)_3^-$.

9. A catalytic composition according to claim 1, wherein the molar ratio of the Bronsted acid to the ionic liquid is 0.001/1 to 30/1.

10. A catalytic composition according to claim 1 further comprising at least one Lewis acid that is soluble in the ionic liquid.

11. A catalytic composition according to claim 10, wherein said Lewis acid is selected from the group consisting of the scandium tris-trifluoromethylsulfonate, ytterbium tris-trifluoromethylsulfonate, scandium tris(bis-trifluoromethanesulfonyl-amide), aluminum trichloride, zirconium tetrachloride, titanium trichloride, triphenylboron, boron trifluoride and antimony pentafluoride.

12. A catalytic composition according to claim 10, wherein the concentration of said Lewis acid in the ionic liquid is 1 to 500 mmol of Lewis acid compound per liter of ionic liquid.

13. A composition according to claim 1, wherein HB is present in an amount sufficient to increase the activity of the catalyst.

14. A composition according to claim 1, wherein HB is present in an amount sufficient to increase the selectivity of the catalyst.

15. A catalytic composition, produced by a process comprising dissolving at least one Bronsted acid, designated HB, in a non-aqueous liquid medium with an ionic nature of general formula $Q^+A^-$, in which $A^-$ represents an anion that is identical to the anion B, and $Q^+$ represents at least one compound of the formula $-NR^1R^2R^3R^{4+}$, $PR^1R^2R^3R^{4+}$, $R^1R^2N=CR^3R^{4+}$ and $R^1R^2P=CR^3R^{4+}$, where $R^1$, $R^2$, $R^3$ and $R^4$, identical or different, represent hydrogen or hydrocarbyl radicals having 1 to 12 carbon atoms with the exception, for $NR^1R^2R^3R^{4+}$, only one of $R^1$, $R^2$, $R^3$ and $R^4$ substituents represents hydrogen, a quaternary ammonium and/or phosphonium cation derived from nitrogenous or phosphorus heterocyclic compounds comprising 1, 2 or 3 nitrogen atoms and/or phosphorus atoms, of the formula:

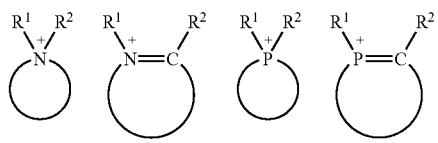

in which the cycles consist of 4 to 10 atoms, wherein $R^1$ and $R^2$ are defined as above;

a quaternary ammonium and/or phosphonium cation of formula:

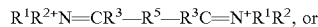

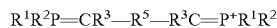

in which $R^1$, $R^2$ and $R^3$, identical or different, are defined as above, and $R^5$ represents an alkylene radical or a phenylene radical or $SR^1R^2R^{3+}$, wherein $R^1$, $R^2$ and $R^3$, identical or different, represent hydrocarbyl radicals that have 1 to 12 carbon atoms.

16. A catalytic composition according to claim 15, wherein the molar ratio of the Bronsted acid to the ionic liquid is between 0.001/1 and 1/1.

17. A catalytic composition according to claim 15 further comprising at least one Lewis acid that is soluble in the ionic liquid.

18. A process for the alkylation of an aromatic hydrocarbon by an olefin, comprising contacting said aromatic hydrocarbon and olefin in the presence of an acid catalyst comprising a catalytic composition according to claim 1.

19. A process for alkylation of an aromatic hydrocarbon according to claim 18, wherein the olefin has a number of carbon atoms from 2 to 20.

20. A process for alkylation of an aromatic hydrocarbon according to claim 18, at a molar ratio between the olefin and the aromatic hydrocarbon of from 0.05/1 to 100/1.

21. A process for alkylation of an aromatic hydrocarbon according to claim 18, conducted at autogenous pressure or at a pressure ranging up to 100 MPa.

22. A process for alkylation of an aromatic hydrocarbon according to claim 18, wherein the catalytic composition further comprises at least one Lewis acid.

23. A process for the dimerization of isobutene, comprising contacting isobutene with an acid catalyst comprising a catalytic composition according to claim 1.

24. A process for dimerization of isobutene according to claim 23, wherein the catalytic composition, has a molar ratio of the Bronsted acid HB to ionic liquid $Q^+A^-$ of from 0.001/1 to 0.1/1.

25. A process for dimerization of the isobutene according to claim 23, wherein the dimerization reaction is carried out in the presence of an alcohol or an ether.

26. A process for dimerization of isobutene according to claim 23, is conducted by reactive distillation.

27. A process for dimerization of isobutene according to claim 23 further comprising reacting the isobutene by hydrogenation, hydroformylation, oxidation, etherification, epoxidation or hydration.

28. A process for the oligomerization of olefins, comprising contacting said olefins with an acid catalyst comprising catalytic composition according to claim 1.

29. A process for oligomerization of olefins according to claim 28, wherein the catalyst has a molar ratio of the Bronsted acid to ionic liquid of 0.1/1 to 1/1.

30. A process for oligomerization of olefins according to claim 27, wherein the catalytic composition further comprises at least one Lewis acid.

31. A process for the alkylation of at least one olefin with an isoparaffin to produce paraffinic hydrocarbons, comprising contacting said olefin and isoparaffin with an acid catalyst comprising a catalytic composition according to claim 1.

32. A process for alkylation of at least one olefin with an isoparaffin according to claim 31, wherein the isoparaffin is isobutane, methyl-2 butane, methyl-2- pentane or methyl-3-pentane, the olefin is ethylene, propylene, an n-butene, isobutene, an n-pentene or an isopentene, wherein the isoparaffin and the olefin are in a molar ratio of 2/1 to 100/1.

33. A process for alkylation of at least one olefin with an isoparaffin according to claim 31, wherein the catalyst has a the molar ratio of the Bronsted acid to ionic liquid of 1/1 to 30/1.

34. A process for alkylation of at least one olefin with an isoparaffin according to claim 31, wherein the catalytic composition further comprises at least one Lewis acid.

35. A process for alkylation of at least one olefin with an isoparaffin according to claim 31, at a reaction temperature of from −20° C. to +30° C.

36. A process for isomerization of n-paraffins into isoparaffins, comprising contacting said n-paraffins with an acid catalyst comprising a catalytic composition according to claim 1.

37. A process for the isomerization of n-olefins into iso-olefins comprising contacting said n-olefins with an acid catalyst comprising a catalytic composition according to claim 1.

38. A process for the comprising isomerization of a double bond of an olefin, comprising contacting said olefin with an acid catalyst comprising a catalytic composition according to claim 1.

39. A process for isomerization of the double bond of an olefin according to claim 38, wherein at least one olefin has 4 to 30 carbon atoms.

40. A process for isomerization of the double bond of an olefin according to claim 38, wherein the catalyst has a molar ratio of the Bronsted acid to the ionic liquid of 0.001 to 1/1.

41. A process for isomerization of a double bond of an olefin according to claim 38, wherein the reaction is conducted by reactive distillation.

42. A process for the purification of an olefin mixture that contains branched alpha olefins as impurities, comprising contacting said mixture with an acid catalyst comprising a catalytic composition according to claim 1.

43. A process for purification of an olefin mixture according to claim 42, wherein the olefin mixture has 4 to 30 carbon atoms.

44. A process for purification of an olefin mixture according to claim 42, wherein the catalyst has a molar ratio of the Bronsted acid to the ionic liquid of 0.001 to 0.1/1.

45. A process for purification of an olefin mixture according to claim 42 is conducted by reactive distillation.

* * * * *

UNITED STATES PATENT AND TRADEMARK OFFICE
CERTIFICATE OF CORRECTION

PATENT NO. : 7,256,152 B2  
APPLICATION NO. : 10/232837  
DATED : August 14, 2007  
INVENTOR(S) : Helene Olivier-bourbigou et al.

It is certified that error appears in the above-identified patent and that said Letters Patent is hereby corrected as shown below:

Column 17, line 60, reads "quatemary" should read -- quaternary --  
Column 17, line 67, reads "$R^2,R^3$" should read -- $R^2, R^3$ --  
Column 18, line 20, reads "quatemary" should read -- quaternary --  
Column 18, line 31, reads "N-ethylpyridiniurn," should read -- N-ethylpyridinium, --  
Column 18, line 62, reads "bis-trifluorornethanesulfonyl" should read  
-- bis-trifluoromethanesulfonyl --  
Column 19, line 36, reads "quatemary" should read -- quaternary --  
Column 19, line 51, reads "quatemary" should read -- quaternary --  
Column 20, line 27, reads "dirnerization" should read -- dimerization --  
Column 20, line 28, reads "23, is conducted" should read -- 23, conducted --  
Column 20, line 41, reads "claim 27," should read -- claim 28, --  
Column 20, line 56, reads "the molar ratio" should read -- molar ratio --  
Column 21, line 5, reads "for the comprising " should read -- for the --  
Column 22, line 15, reads "42 is conducted" should read -- 42 conducted --

Signed and Sealed this

Twenty-sixth Day of February, 2008

JON W. DUDAS  
*Director of the United States Patent and Trademark Office*